United States Patent [19]

Perrone

[11] 4,241,499
[45] Dec. 30, 1980

[54] FOOT CARE INSTRUMENT

[76] Inventor: Michael A. Perrone, 4103 Hillsboro Cir., Nashville, Tenn. 37215

[21] Appl. No.: 49,932

[22] Filed: Jun. 19, 1979

[51] Int. Cl.³ ............................................. A45D 29/18
[52] U.S. Cl. ........................................ 30/27; 132/75.4
[58] Field of Search ................... 30/27, 26; 7/162; 132/75.4

[56] References Cited

U.S. PATENT DOCUMENTS

| | | | |
|---|---|---|---|
| 1,016,343 | 2/1912 | Makarhof | 30/27 |
| 2,524,102 | 10/1950 | Freudenberger | 30/27 X |
| 2,801,640 | 8/1957 | Steele | 132/75.4 |
| 3,600,803 | 8/1971 | Nachsi | 30/27 |

FOREIGN PATENT DOCUMENTS 907702  6/1945  France .......................... 30/26

*Primary Examiner*—Jimmy C. Peters
*Attorney, Agent, or Firm*—Clarence A. O'Brien; Harvey B. Jacobson

[57] ABSTRACT

An elongated handle having top and bottom surfaces and defining front and rear end portions. The handle includes top and bottom surfaces and opposite side surfaces as well as a transversely enlarged head on the front end thereof. The head includes a longitudinally convex bowed and generally transversely straight bottom surface portion and a central upstanding opening is formed through the head and opens upwardly through the top surface of the handle and downwardly through the bottom surface portion rearwardly of the front end of the head. A transverse roller is journaled in the opening between the front and rear limits thereof and a cutting blade is supported from the head and defines a rearwardly and downwardly facing straight transverse cutting edge generally flush with the aforementioned undersurface portion and spaced intermediate the roller and the forward extremity of the opening.

11 Claims, 4 Drawing Figures

U.S. Patent     Dec. 30, 1980     4,241,499
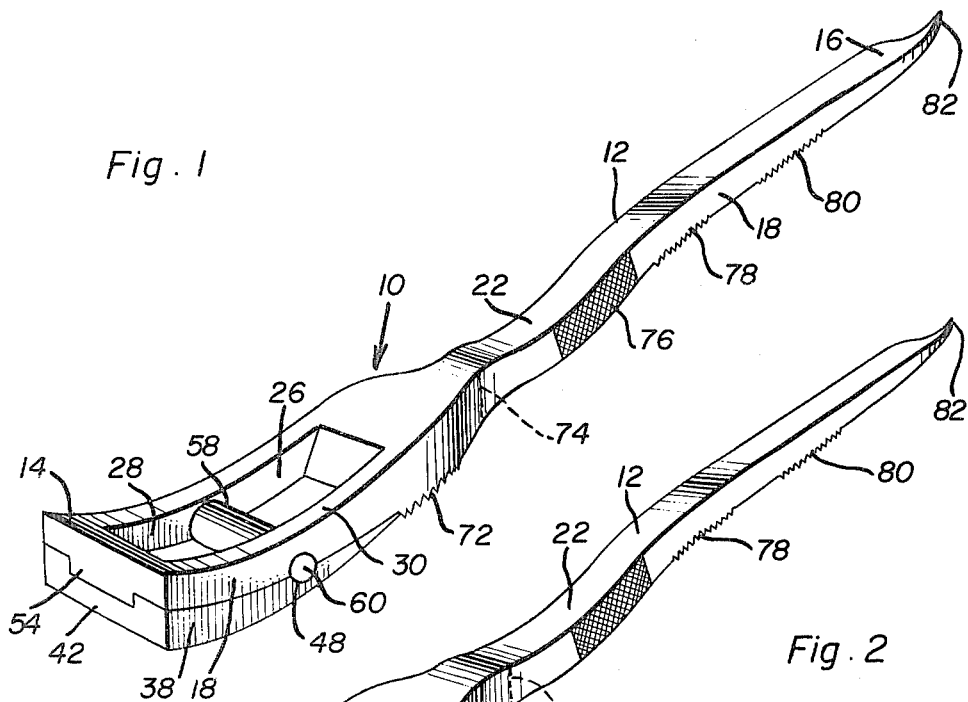
Fig. 1
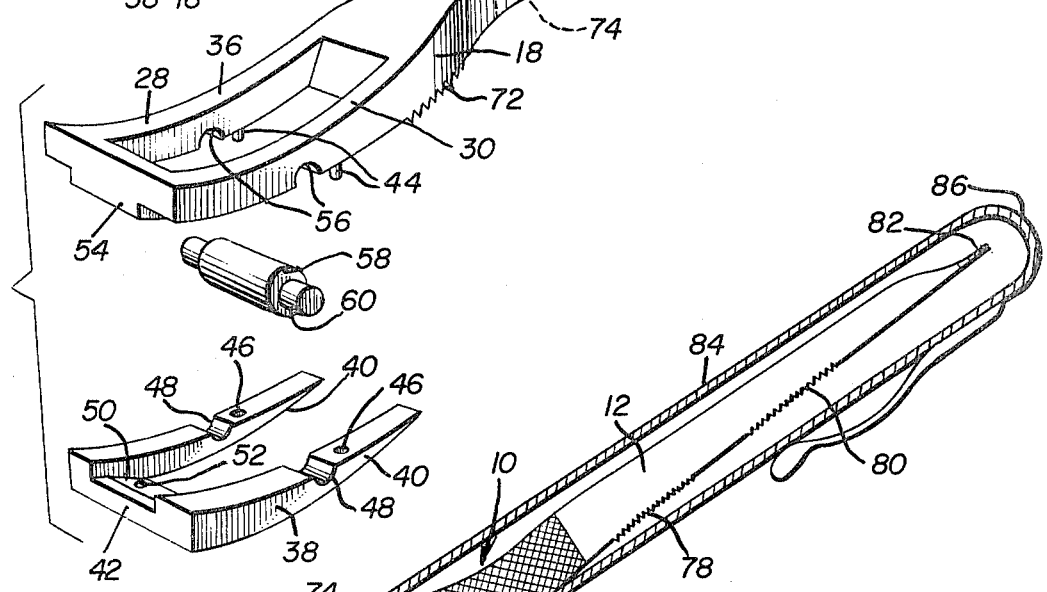
Fig. 2
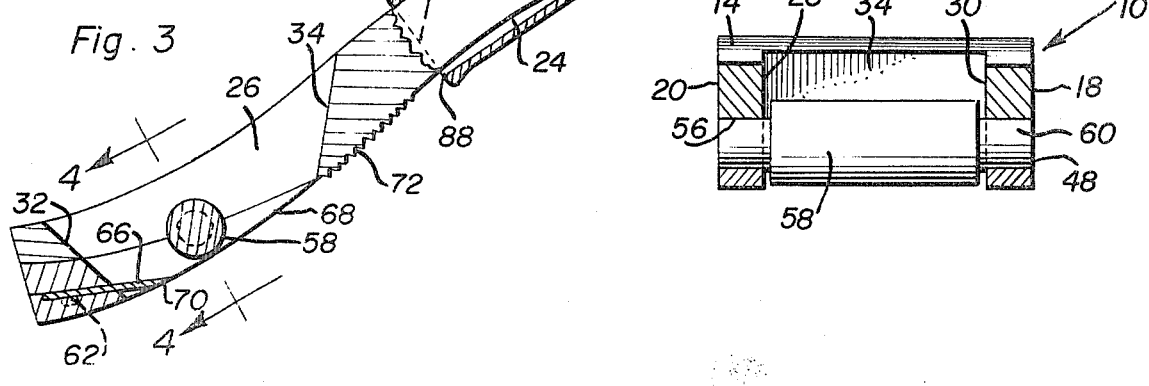
Fig. 3
Fig. 4

FOOT CARE INSTRUMENT

BACKGROUND OF THE INVENTION

There are various areas of the feet of some persons upon which thickened and hardened skin forms. While some of these areas of thickened and hardened skin may be relieved through the utilization of special pads, many thickened and hardened skin areas of the feet may be successfully removed only by cutting or slicing successive thin layers of skin from the affected area.

Although various forms of corn and callous shavers or trimmers have been heretofore provided, such as those disclosed in U.S. Pat. Nos. 861,836, 1,239,419, 2,612,683, 3,600,803, 3,636,625 and 3,797,505, most of these cutters and trimmers are constructed in a manner whereby even thin and substantially constant thickness layers of skin may not be readily sliced from the surrounding skin area. Accordingly, a need exists for an apparatus whereby even thickness layers of calloused skin, and the like, may be successively removed from various body portions, such as those which may be found on the feet and other body portions.

SUMMARY OF THE INVENTION

The foot care instrument of the instant invention defines an elongated handle including an enlarged head on one end through which an upstanding opening is formed. A tranverse roller is journaled in the opening centrally intermediate the side limits of the opening opposing opposite sides of the roller and with the outer periphery of the roller spaced, only slightly, above of the lower end of the opening. The undersurface of the head through which the lower end of the opening exits is transversely straight, but longitudinally convexly bowed, and a cutting blade is supported from the head and includes a cutting edge extending transversely of the opening intermediate the roller and the limit of the opening remote from the far end of the handle. The cutting edge is formed on a blade inclined approximately 5° to 15° relative to the adjacent convex undersurface of the head. The elongated handle includes a roughened dermabrasion undersurface portion immediately adjacent the opening and additional longitudinally spaced outwardly facing roughened surfaces to function as a nail file and a skin smoother. Also, the end of the handle remote from the head end thereof includes a tapered end portion which may be utilized for cleaning nails and pushing back cuticles. Also, the handle, at its root end adjacent the head, includes a weakened zone by which the handle may be broken from the head and the breakaway handle portion is provided with a closure cap removably telescoped thereover. In this manner, when the cutting edge of the foot care instrument becomes dull and it is necessary that a new instrument be purchased, the breakaway handle portion may be saved and utilized as a supplemental skin and nail instrument.

The main object of this invention is to provide a foot care instrument including structure by which roughened and calloused skin areas may be sliced from adjacent skin portions in thin even thickness layers.

Another object of this invention is to provide an instrument in accordance with the preceding object and constructed in a manner whereby certain skin areas may be abraded away.

Yet another object of this invention is to provide an instrument including nail file surface defining portions thereof.

Another object of this invention is to provide an instrument also including an end portion thereof suitable for cleaning finger nails and also suitable for pushing back cuticles.

A further very important object of this invention is to provide an instrument in accordance with the preceding objects and including a breakaway handle portion which may be utilized as a supplemental nail and skin tool when it becomes necessary to replace the skin slicing portion of the instrument.

A final object of this invention to be specifically enumerated herein is to provide a foot care instrument in accordance with the preceding objects and which will conform to conventional forms of manufacture, be of simple construction and easy to use so as to provide a device that will be economically feasible, long lasting and relatively trouble-free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a perspective view of the instrument of the instant invention;

FIG. 2 is an exploded perspective view of the instrument;

FIG. 3 is an enlarged longitudinal vertical sectional view of the instrument and with a cap-type container engaged over the breakaway handle portion of the instrument; and FIG. 4 is a transverse sectional view taken substantially upon the plane indicated by the section line 4—4 of FIG. 3.

DESCRIPTION OF THE PREFERRED EMBODIMENTS

Referring more specifically to the drawings, the numeral 10 generally designates the foot care instrument of the instant invention. The instrument 10 includes an elongated handle 12 defining front and rear end portions 14 and 16. The handle 12 includes opposite side surfaces 18 and 20 and top and bottom surfaces 22 and 24.

The front end portion 14 is transversely enlarged and has an upstanding opening 26 formed therethrough including opposite side walls 28 and 30 and front and rear extremities 32 and 34.

The head or front end portion 14 includes superposed upper and lower sections 36 and 38 which are separately formed, the section 36 being integral with the remainder of the handle 12. The section 38 is generally U-shaped in horizontal plan including a pair of generally parallel opposite side portions 40 interconnected at their forward ends by an integral bight portion 42. The side walls 28 and 30 include downwardly projecting pegs 44 seated in upwardly opening bores 46 formed in the opposite side portions 40. Also, the opposite side portions 40 include upwardly opening semi-cylindrical journal portions 48 and the bight portion, although reduced in vertical thickness relative to the adjacent portions of the opposite side portions 40, includes a recess 50 formed therein upwardly through which a pair of bores 52 corresponding to the bores 46 open.

The reduced vertical thickness of the bight portion 42, relative to the vertical thickness of the opposite side portions 40, defines a front to rear extending channel and the upper section 36 includes a depending rib 54 which is seatingly receivable in the channel and the side walls 28 and 30 include aligned downwardly opening semi-cylindrical journal portions 56 with which the journal portions 48 are registrable.

A roller 58 including diametrically reduced opposite end portions 60 is provided and the forward end portion of the upper section 36 includes depending pins 62 corresponding to the pegs 44. The lower section 38 is upwardly seated against the underside of the upper section 36 with the pins 44 seated in the bores 46, the rib 54 seated in the channel between the forward ends of the side walls 28 and 30 and the pins 62 seated in the bores 52. In addition, a cutting blade 66 is seated in the recess 50 and has openings (not shown) formed therein through which the pins 62 project. The pegs 44 and pins 62 are secured in the bores 46 and 52 by chemical or sonic welding processes, the sections 36 and 38 being constructed of plastic, and in this manner the cutting blade 66 is securely fastened in position between the opposing surfaces of the upper and lower sections 36 and 38.

The blade 66 is inclined between 5° and 15° relative to the undersurface 68 of the head defining forward end portion, the undersurface 68 being defined entirely by the lower section 38. The diametrically reduced opposite end portions 60 of the roller 58 are journaled in the journal portions 48 and 56 and accordingly, the roller 58 is journaled within the opening 26 between the side walls 28 and 30 thereof generally centrally intermediate the forward and rear extremities 32 and 34 of the opening 26. The blade 66 includes a cutting edge 70 which is substantially straight and extends transversely across the opening 26. Also, the edge 70 lies substantially in the same plane as the convexly arched and transversely straight undersurface 68 of the lower section 38, generally midway between the lower peripheral portion of the roller 58 and the forward extremity 32 of the opening 26. Further, it will be noted that the lower periphery of the roller 58 is spaced, slightly, above the convexly arched undersurface 68.

When the tool 10 is grasped by the handle 12 remote from the head defining forward end portion 14 and drawn rearwardly over a thickened or calloused skin area, the skin is elevated into the opening 26 forward of roller 58 and is thereafter engaged and depressed by the roller 58 prior to engagement of the skin by the cutting edge 70 to insure uniform elevation of the skin toward the edge 70 and thus enable the cutting or slicing of a thin constant thickness layer from the thickened skin area. Of course, downward pressure on the handle to force the head end portion 14 into tighter contact with the affected skin area results in a thicker slice of skin being cut from the affected area.

The convex curvature of the undersurface 68 of the head end portion 14 is extremely important, in conjunction with the roller 58, in that a more controlled thickness of the slices of skin to be removed is enabled.

The rear end head end portion 14 includes a roughened dermabrasion undersurface portion 72 and the head end portion 14 is joined to the remainder of the handle 12 by a weakened area 74 of the handle 12 and accordingly, the head end portion 14 may be readily broken from the remainder of the handle 12 when the cutting edge 70 becomes dull. The breakaway handle portion includes a surface portion 76 thereof which defines a nail filing surface and which may be molded into the plastic material of which the handle 12 is constructed or may be applied to the handle 12 in the form of sandpaper or metal file. In addition, additional roughened surface portions 78 and 80 are spaced along the length of the breakaway handle portion and the rear end portion 16 of the handle 12 terminates in a tapered end portion 82 which may be utilized to clean a persons nails or to push back cuticle areas. Further, with attention invited more specifically to FIG. 3 of the drawings, a tubular cap 84 is provided and is closed at one end 86 while being opened at the other end 88. The open end of the cap 84 may be frictionally telescoped over the breakaway portion of the handle 12 and in this manner the breakaway portion of the handle 12 may be used for nail cleaning, filing, and cuticle pushing purposes long after the edge 70 has become dulled and no longer efficiently usable. Of course, if there is no need to continue slicing layers of skin from thickened or calloused skin areas, there is no need to buy a replacement instrument 10. On the other hand, if more skin slicing is required, another replacement instrument may be purchased and the breakaway portion of the handle 12 of the original instrument may be utilized as a supplemental instrument.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A multipurpose foot car instrument including an elongated handle defining front and rear ends and having top and bottom surfaces and opposite side surfaces as well as a transversely enlarged head on said front end of said handle, said head including a longitudinally convexly bowed and generally transversely straight bottom surface portion and defining a central upstanding opening extending therethrough opening upwardly through said top surface and downwardly through said bottom surface portion rearward of said front end, skin depressing and guide structure journaled in said opening between the front and rear limits of said opening, and a cutting blade supported from said head and defining a rearwardly and downwardly facing straight transverse cutting edge generally flush with said undersurface portion spaced intermediate said skin depressing and guide structure and the forward extremity of said opening and at least substantially entirely spanning the latter.

2. The combination of claim 1 wherein said bottom surface includes a roughened skin abrasive portion between the rear extremity of said opening and the rear extremity of said head.

3. The combination of claim 1 wherein said head includes superposed upper and lower section, said bottom surface portion being defined by said lower section, said sections being secured together against separation, opposing opposite side portions of said upper and lower sections defining said opening including registered one-half journal portions, said skin depressing and guide structure including a generally cylindrical roller having diametrically reduced opposite end portions journaled in said one-half journal portions.

4. The combination of claim 1 wherein said head includes superposed upper and lower sections, said bottom surface portion being defined by said lower section, said sections being secured together against separation, at least one of said sections including a recess in the surface portions thereof opposing the other section and opening into said opening, said cutting blade being captively seated in said recess.

5. The combination of claim 4 wherein opposing opposite side portions of said upper and lower sections include registered one-half journal portions, said skin depressing and guide structure including a generally cylindrical roller having diametrically reduced opposite end portions journaled in said one-half journal portions.

6. The combination of claim 5 wherein the opposing under and upper surface portions of said sections include interfittingly engaged rib and channel defining portions extending lengthwise of said handle between the front end thereof and said upstanding opening.

7. The combination of claim 1 wherein said rear end of said handle includes longitudinally spaced roughened abrasive surfaces thereon.

8. The combination of claim 7 wherein the last mentioned surfaces of said handle are formed on at least one side and bottom surfaces of said handle.

9. The combination of claim 1 wherein said rear end of said handle terminates in a tapered tip for pushing cuticles and cleaning finger nails.

10. The combination of claim 9 wherein said handle includes a weakened zone closely adjacent the juncture of the rear portion of said head and the remainder of said handle.

11. The combination of claim 10 including a tubular cap open at one end and in which said remainder of said handle is removably telescopingly receivable.

* * * * *